(12) United States Patent
Kastenhofer

(10) Patent No.: US 7,635,347 B2
(45) Date of Patent: *Dec. 22, 2009

(54) CATHETER WITH MULTILAYER TUBE

(75) Inventor: Gerhard Kastenhofer, Effretikon (CH)

(73) Assignee: Schneider (Europe) A.G., Bulach (CH)

( * ) Notice: Subject to any disclaimer, the term of this patent is extended or adjusted under 35 U.S.C. 154(b) by 533 days.

This patent is subject to a terminal disclaimer.

(21) Appl. No.: 11/229,301

(22) Filed: Sep. 16, 2005

(65) Prior Publication Data

US 2006/0015064 A1    Jan. 19, 2006

Related U.S. Application Data

(60) Continuation of application No. 10/280,879, filed on Oct. 25, 2002, now Pat. No. 6,960,187, which is a continuation of application No. 09/317,293, filed on May 24, 1999, now Pat. No. 6,471,673, which is a continuation of application No. 08/936,352, filed on Sep. 24, 1997, now Pat. No. 5,961,765, which is a division of application No. 08/657,004, filed on May 28, 1996, now abandoned, which is a continuation of application No. 08/309,234, filed on Sep. 20, 1994, now abandoned.

(30) Foreign Application Priority Data

Oct. 27, 1993  (EP)  .................... 93117403

(51) Int. Cl.
*A61M 29/00* (2006.01)

(52) U.S. Cl. ................. 604/103.06; 604/96.01

(58) Field of Classification Search .................. 604/523, 604/525, 264, 96.01–103.14; 600/433, 435; 606/192, 194; 428/36.91, 35.2, 36, 91; 153/242, 153/293, 294, 244.11, 244.12
See application file for complete search history.

(56) References Cited

U.S. PATENT DOCUMENTS 3,561,493 A    2/1971    Maillard et al.
(Continued)

FOREIGN PATENT DOCUMENTS

CA    2078201 A1    12/1992
(Continued)

OTHER PUBLICATIONS

Norman G. Gaylord et al., "Compatibilizing Agents: Structure and Function in Polyblends," J. Macromol. Sci.-Chem., A26(8), pp. 1211-1229 (1989).
(Continued)

*Primary Examiner*—Matthew F DeSanto
(74) *Attorney, Agent, or Firm*—Crompton, Seager & Tufte, LLC

(57) ABSTRACT

An interventional catheter for angioplasty and the like, including a catheter tube including an outer tubular member, an inner tubular member disposed within the lumen of the outer tubular member, and a balloon attached to the distal end of the outer tubular member and the distal end of the inner tubular member. The outer tubular member includes a first portion having a first stiffness and a second portion having a second stiffness less than the first stiffness. The inner tubular member has an inner surface having a first coefficient of friction and an outer surface having a second coefficient of friction greater than the first coefficient of friction.

19 Claims, 1 Drawing Sheet

U.S. PATENT DOCUMENTS

| | | | |
|---|---|---|---|
| 3,618,614 A | 11/1971 | Flynn |
| 3,695,921 A | 10/1972 | Shepherd et al. |
| 3,814,137 A | 6/1974 | Martinez |
| 3,890,976 A | 6/1975 | Bazell et al. |
| 4,157,932 A | 6/1979 | Hirata |
| 4,171,416 A | 10/1979 | Motegi et al. |
| 4,211,741 A | 7/1980 | Ostoich |
| 4,265,848 A | 5/1981 | Rüsch |
| 4,282,876 A | 8/1981 | Flynn |
| 4,323,071 A | 4/1982 | Simpson et al. |
| 4,335,723 A | 6/1982 | Patel |
| 4,413,989 A | 11/1983 | Schjeldahl et al. |
| 4,596,563 A | 6/1986 | Pande |
| 4,597,755 A | 7/1986 | Samson et al. |
| 4,627,844 A | 12/1986 | Schmitt |
| 4,636,346 A | 1/1987 | Gold et al. |
| 4,646,719 A | 3/1987 | Neuman et al. |
| 4,702,252 A | 10/1987 | Brooks et al. |
| 4,707,389 A | 11/1987 | Ward |
| 4,729,914 A | 3/1988 | Kliment et al. |
| 4,744,366 A | 5/1988 | Jang |
| 4,762,129 A | 8/1988 | Bonzel |
| 4,763,654 A | 8/1988 | Jang |
| 4,769,099 A | 9/1988 | Therriault et al. |
| 4,775,371 A | 10/1988 | Mueller, Jr. |
| 4,776,849 A | 10/1988 | Shinno et al. |
| 4,782,834 A | 11/1988 | Maguire et al. |
| 4,820,349 A | 4/1989 | Saab |
| 4,863,449 A | 9/1989 | Therriault et al. |
| 4,900,314 A | 2/1990 | Quackenbush |
| 4,906,244 A | 3/1990 | Pinchuk et al. |
| 4,921,483 A | 5/1990 | Wijay et al. |
| 4,923,450 A | 5/1990 | Maeda et al. |
| 4,940,179 A | 7/1990 | Soni |
| 4,955,895 A | 9/1990 | Sugiyama et al. |
| 4,960,410 A | 10/1990 | Pinchuk |
| 4,976,690 A | 12/1990 | Solar et al. |
| 4,976,720 A | 12/1990 | Machold et al. |
| 4,981,478 A | 1/1991 | Evard et al. |
| 4,994,018 A | 2/1991 | Saper |
| 4,994,032 A | 2/1991 | Sugiyama et al. |
| 4,994,047 A | 2/1991 | Walker et al. |
| 5,006,119 A | 4/1991 | Acker et al. |
| 5,026,377 A | 6/1991 | Burton et al. |
| 5,035,694 A | 7/1991 | Kasprzyk et al. |
| 5,041,089 A | 8/1991 | Mueller et al. |
| 5,041,100 A | 8/1991 | Rowland et al. |
| 5,047,045 A | 9/1991 | Arney et al. |
| 5,059,269 A | 10/1991 | Hu et al. |
| 5,063,018 A | 11/1991 | Fontirroche et al. |
| 5,078,727 A | 1/1992 | Hannam et al. |
| 5,085,649 A | 2/1992 | Flynn |
| 5,100,381 A | 3/1992 | Burns |
| 5,100,386 A | 3/1992 | Inoue |
| 5,114,423 A | 5/1992 | Kasprzyk et al. |
| 5,120,323 A | 6/1992 | Shockey et al. |
| 5,147,315 A | 9/1992 | Weber |
| 5,195,969 A | 3/1993 | Wang et al. |
| 5,195,971 A | 3/1993 | Sirhan |
| 5,221,270 A | 6/1993 | Parker |
| 5,234,416 A | 8/1993 | Macaulay et al. |
| 5,250,069 A * | 10/1993 | Nobuyoshi et al. .......... 606/192 |
| 5,254,090 A | 10/1993 | Lombardi et al. |
| 5,267,959 A | 12/1993 | Forman |
| 5,270,086 A | 12/1993 | Hamlin |
| 5,272,012 A | 12/1993 | Opolski |
| 5,279,560 A | 1/1994 | Morrill et al. |
| 5,290,230 A | 3/1994 | Ainsworth et al. |
| 5,290,306 A | 3/1994 | Trotta et al. |
| 5,304,134 A | 4/1994 | Kraus et al. |
| 5,338,299 A | 8/1994 | Barlow |
| 5,348,536 A | 9/1994 | Young et al. |
| 5,356,709 A | 10/1994 | Woo et al. |
| 5,383,853 A | 1/1995 | Jung et al. |
| 5,397,306 A | 3/1995 | Nobuyoshi et al. |
| 5,403,292 A | 4/1995 | Ju |
| 5,405,338 A | 4/1995 | Kranys |
| 5,409,495 A | 4/1995 | Osborn |
| 5,423,754 A | 6/1995 | Cornelius et al. |
| 5,425,712 A | 6/1995 | Goodin |
| 5,439,454 A | 8/1995 | Lo et al. |
| 5,460,608 A | 10/1995 | Lodin et al. |
| 5,478,320 A | 12/1995 | Trotta |
| 5,484,444 A | 1/1996 | Braunschweiler et al. |
| 5,499,973 A | 3/1996 | Saab |
| 5,501,759 A | 3/1996 | Forman |
| 5,514,236 A | 5/1996 | Avellant et al. |
| 5,527,281 A | 6/1996 | Haas |
| 5,533,985 A | 7/1996 | Wang |
| 5,538,510 A | 7/1996 | Fontirroche et al. |
| 5,545,151 A | 8/1996 | O'Connor et al. |
| 5,549,552 A | 8/1996 | Peters et al. |
| 5,558,737 A | 9/1996 | Brown et al. |
| 5,562,127 A | 10/1996 | Fanselow et al. |
| 5,571,089 A | 11/1996 | Crocker |
| 5,620,649 A | 4/1997 | Trotta |
| 5,643,209 A | 7/1997 | Fugoso et al. |
| 5,653,691 A | 8/1997 | Rupp et al. |
| 5,676,659 A | 10/1997 | McGurk |
| 5,728,063 A | 3/1998 | Preissman et al. |
| 5,728,088 A | 3/1998 | Magruder et al. |
| 5,733,400 A | 3/1998 | Gore et al. |
| 5,749,852 A | 5/1998 | Schwab et al. |
| 5,792,814 A | 8/1998 | Oishi et al. |
| 5,797,877 A | 8/1998 | Hamilton et al. |
| 5,820,594 A | 10/1998 | Fontirroche et al. |
| 5,824,173 A | 10/1998 | Fontirroche et al. |
| 5,837,313 A | 11/1998 | Ding et al. |
| 5,843,032 A | 12/1998 | Kastenhofer |
| 5,961,765 A | 10/1999 | Kastenhofer |
| 6,027,477 A | 2/2000 | Kastenhofer |
| 6,319,228 B1 | 11/2001 | Kastenhofer |
| 6,471,673 B1 * | 10/2002 | Kastenhofer ............ 604/103.06 |
| 6,960,187 B2 * | 11/2005 | Kastenhofer ............ 604/103.06 |

FOREIGN PATENT DOCUMENTS

| | | |
|---|---|---|
| EP | 0 277 368 A1 | 8/1988 |
| EP | 0 279 959 B1 | 8/1988 |
| EP | 0 298 634 A1 | 1/1989 |
| EP | 0 351 687 A2 | 1/1990 |
| EP | 0 358 117 B1 | 3/1990 |
| EP | 0 380 102 A1 | 8/1990 |
| EP | 0 420 488 A1 | 4/1991 |
| EP | 0 436 501 B1 | 7/1991 |
| EP | 0 452 123 A1 | 10/1991 |
| EP | 0 456 342 A1 | 11/1991 |
| EP | 0 520 692 A1 | 12/1992 |
| EP | 0 530 201 B1 | 3/1993 |
| EP | 0 650 740 A1 | 5/1995 |
| EP | 0 669 142 A2 | 8/1995 |
| EP | 0 803 264 A1 | 10/1997 |
| GB | 2 130 093 A | 5/1984 |
| GB | 2 209 121 A | 5/1989 |
| WO | WO 89/02763 A1 | 4/1989 |
| WO | WO 92/11893 A1 | 7/1992 |
| WO | WO 93/05842 A1 | 4/1993 |
| WO | WO 95/18647 A2 | 7/1995 |

OTHER PUBLICATIONS

Brochure: "ASUKA™ 2.9F OTW PTCA Balloon Catheter," Feb. 1994.

"Physical Constants of Important Polymers," Polymer Handbook, 2nd Edition, A Wiley-Interscience Publication, 1975, p. V-13 thru V-22.

"Physical Constants of Poly(Vinyl Chloride)," Polymer Handbook, 2nd Edition, A Wiley-Interscience Publication, 1975, p. V-41 thru V-50.

"Abrasion & Wear," Encyclopedia of Polymer Science and Engineering, vol. 1, A to Amorphous Polymers, A Wiley-Interscience Publication, 1985, pp. 1-35.

Brochure: "Opti-Plast PTA Balloon Dilatation Catheters: for Peripheral Angioplasty," Vas-Cath Incorporated, 4 pages (1991).

PLEXAR® PX 360 (2 pages).

PLEXAR® PX 209 (2 pages).

PLEXAR® Tie-Layer Resins, Products, Applications, and Key Properties (3 pages).

Quantum Chemical Corporation Material Safety Data Sheet PLEXAR™ (5 pages).

Chevron Chemical Company Technical Data Sheet Ethylene-Methyl Acrylate Copolymer EMAC SP 2260 (2 pages).

Chevron Chemical Company Technical Data Sheet Ethylene-Methyl Acrylate Copolymer EMAC SP 2205 (2 pages).

Bynel® Coextrudable Adhesive Resins Selector Guide (6 pages).

DuPont Hytrel® Polyester Elastomer Hytrel 7246 (2 pages).

DSM Engineering Plastics Arnitel®—Available Grades List (4 pages).

Petrothene® LS 5060-00 (1 page).

Petrothene® LM 6007-00 (1 page).

Norman G. Gaylord et al., "Maleation of Linear Low-Density Polyethylene by Reactive Processing," *Journal of Applied Polymer Science*, vol. 44, No. 11, Apr. 15, 1992, pp. 1941-1949.

* cited by examiner

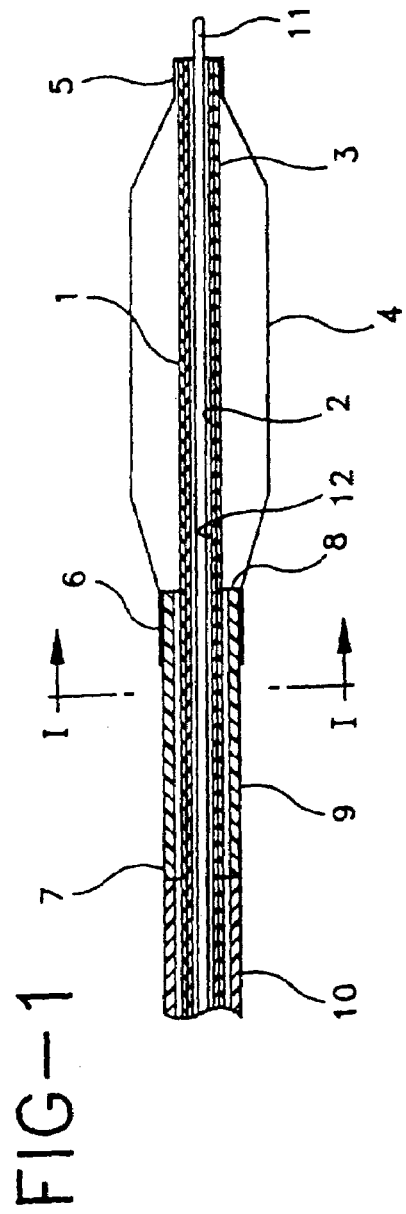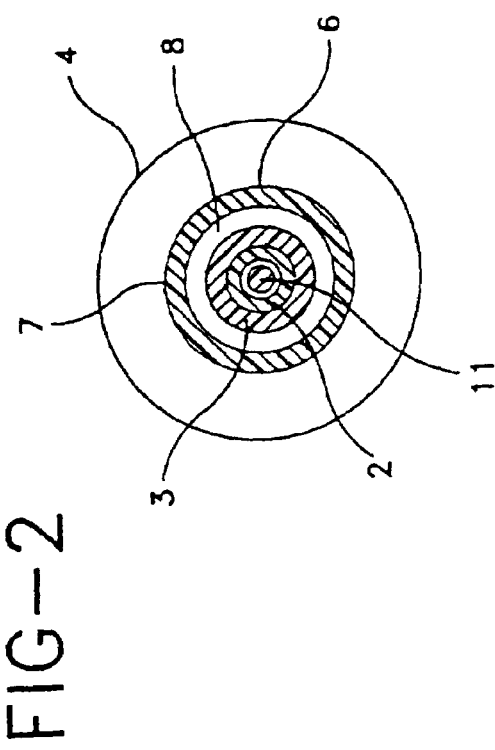

CATHETER WITH MULTILAYER TUBE

CROSS REFERENCE TO CO-PENDING AND RELATED APPLICATIONS

This application is a continuation of U.S. patent application Ser. No. 10/280,879, filed Oct. 25, 2002, now U.S. Pat. No. 6,960,187, the disclosure of which is incorporated herein by reference; which is a continuation of U.S. patent application Ser. No. 09/317,293, filed May 24, 1999, now U.S. Pat. No. 6,471,673; which is a continuation of U.S. patent application Ser. No. 08/936,352, filed Sep. 24, 1997, now U.S. Pat. No. 5,961,765; which is a divisional of U.S. patent application Ser. No. 08/657,004, filed May 28, 1996, abandoned; which is a continuation of U.S. patent application Ser. No. 08/309,234, filed Sep. 20, 1994, abandoned; which claims priority to European Pat. Application No. 93117403.1, filed Oct. 27, 1993.

BACKGROUND OF THE INVENTION

This invention relates to an interventional catheter comprising a catheter tube having two superposed layers of materials secured in relation to one another and with mechanical properties differing from one another, a longitudinal lumen in said catheter tube for the sliding fit of a guide wire, and a balloon with a proximal end and a distal end, whereby the distal end sealingly surrounds said catheter tube, whereby the catheter tube has an inner layer forming the longitudinal lumen and an outer layer forming the outer surface of the catheter tube.

Over the wire catheters are now widely used for interventions such as percutaneous transluminal angioplasty. A problem with these catheters is that the guide wire may clog into the longitudinal lumen of the catheter; as a result, the guide wire may follow the balloon upon withdrawal thereof after the inflation procedure, thereby making it necessary to re-insert the guide wire into the threaded area of the blood vessel for re-positioning a balloon therein in case a second inflation is needed. Apart of this, the catheter has to achieve an acceptable compromise between the requirements of some stiffness to assure good pushability and of some flexibility to assure kink resistance. In addition, the catheter has to permit safe attachment of the balloon to the catheter tube.

The document WO 92/11893 describes an intra-aortic balloon apparatus comprising a hollow catheter in which is located an elongated member forming a central lumen extending out of the catheter at the distal end thereof. An aortic pumping balloon is positioned over the elongated member; the distal end of the balloon is bonded to a tip affixed to the distal end of the elongated member, and its proximal end is bonded to the distal end of the catheter. In order to achieve a balance of flexibility and remains and to avoid kinking, the elongated member is formed of an inner layer comprised of a soft elastomeric material to impart flexibility to the tubing, and the outer layer is comprised of a hard plastic material to impart structural support to the elongated member. The combination of these two layers is made to achieve a very durable and flexible structure exhibiting a low kink radius. This balloon apparatus cannot be loaded with a guidewire and moved into tortuous vessels with the guidewire loaded inside the elongated tube. The friction between the guidewire and the elongated member increases distinctively when the elongated member is shaped into curves. The above procedure would therefore risk that the spiral wound guidewire could be captured in the soft elastomeric plastic material of the inner layer of the elongated member. Although the outer layer of the elongated member that is coextruded onto the inner layer is formed from nylon, a material which is directly weldable to a wide variety of materials, this balloon apparatus cannot be introduced into narrow vessels or narrow stenoses nor can it be passed through narrow punctures to enter the blood vessels. This is because of the relatively large profile of the folded balloon. The large profile is due to the distal fixture of the balloon to the elongated member. The balloon is bonded to an intermediate tip element which in turn is bonded to the elongated member.

U.S. Pat. No. 4,323,071 describes a combination guiding catheter assembly and dilating catheter assembly. The guiding catheter assembly comprises a first flexible tubular member formed of a material with low coefficient of friction and high flexibility; as this first tubular member is too flexible to serve as a guiding catheter because it could not be properly manipulated in the body of a patient, a second tubular member made of a heat shrinkable tubing is provided to encase the first tubular member. The distal end of this assembly is preshaped to form a shape corresponding to the standard coronary catheter and the proximal end of the assembly is provided with attachment means to provide a leak-proof adhesive-free connection. The dilating catheter assembly is disposed within the guiding catheter assembly and comprises a first tubular member coaxially disposed within a second tubular member having formed thereon a balloon at its distal end, both these tubular members being made of shrink tubing; an annular flow passage between the first and second tubular members allows introduction of fluid into the balloon for inflation thereof. The proximal end of this assembly is inserted in an adapter body for connection to an appropriate syringe system. A dilator consisting of a flexible plastic tube with a teflon coated guide wire therein is used to position the guiding catheter assembly in the proper location. Within this frame, the guide wire is first inserted conventionally into the blood vessel; the dilator is then positioned in the guiding catheter assembly to straighten it, and the dilator and guiding catheter are passed over the guide wire into the blood vessel; when the guiding catheter is in the proper location, the dilator and guide wire are withdrawn from the guiding catheter and the dilating catheter assembly can be inserted into the guiding catheter assembly, which operation is facilitated be the low coefficient of friction of the first tubular member of the guiding catheter assembly. A small guide wire may be utilized if necessary to precisely position the balloon of the dilating catheter assembly; if so, this small guide wire has to be inserted into the first tubular member of the dilating catheter assembly so that it extends from the distal portion thereof. This guide wire may be removed once the balloon is in the proper location.

This publication shows a catheter shaft made from a composited material that is achieved by heat shrinking. The material for the inner layer of the composite material is selected from materials rendering low friction. Any instrument inserted into a catheter shaft made from this composite material can easily be moved inside the shaft even after the shaft has been bent and is kept in narrow curves. The shaft for the dilation balloon catheter shown in this publication does not use composite material for its construction. It uses conventional material in one single layer. Because the balloon must be welded or otherwise securely bonded to the catheter shaft to withstand the extraordinary high inflation pressures used in angioplasty, the shaft material for this dilatation balloon catheter has to be selected for good bond characteristics and cannot be selected for good friction characteristics. Therefore this catheter still presents the problem that in tortuous vessels, when the catheter shaft has to follow numerous bends of the vessel, the guidewire can be captured in the shaft. This is specifically troublesome since the dilation catheter has to advance much deeper into the branched vessel system than the guiding catheter which in this publication is shown as made from composite material. For a dilatation catheter the length of the friction creating shaft is longer than the shaft of the guiding catheter and additionally the dilatation catheter shaft is exposed to more vessel curves.

SUMMARY OF THE INVENTION

The purpose of the present invention is to present an interventional low profile balloon catheter that can be moved into tortuous vessels with a guidewire inside the catheter without the risk of the guidewire being captured or clogging in the catheter.

To this effect, the interventional catheter according to the invention complies with the definitions given in the claims.

In that way, there is no more risk of having the guide wire clogging in the longitudinal lumen of the catheter tube, in particular upon withdrawal of the balloon. Withdrawal and re-positioning of a balloon for repeated inflation is therefore rapid, safe and precise, because during withdrawal of the balloon the guidewire can be left in place with the tip of the guidewire at the site of the treatment in the vessel system. As the inner layer forming the longitudinal lumen is separated from the balloon by the outer layer, the choice may be made towards materials having the most appropriate friction and kink resistance coefficients, while safe attachment of the balloon may be made at will on an outer layer of the catheter tube which may be chosen without being influenced by the properties of the inner layer.

The inner layer and the outer layer may be congruent in length so that the catheter shaft can be produced in long tubes which are cut into length to form the individual catheter tube.

Where the two layers of the catheter are produced by extruding the outer layer over the inner layer, a specifically reliable catheter tube is formed in a continuous process. To heat shrink the outer layer onto the inner layer would not allow a continuous process because of the presence of an inner core inside the inner layer. This core has to take up the radial pressure during the heat shrinking process and has to be removed after heat shrinking.

The seal between the balloon and the catheter tube may be achieved by welding the balloon material to the outer layer of the catheter tube. This allows the design of balloon catheters that withstand the extraordinary high inflation pressures used in angioplasty so that these catheters also show the low clogging risk and the low profile given by the invention.

In a preferred form of the invention, the inner layer forming the longitudinal lumen of the catheter tube is made of a polyethylene or of a high density polyethylene, both of which assure an extremely low friction coefficient and an appropriate kink resistance coefficient. In another preferred embodiment, the catheter tube will comprise an outer layer made of a polyamide assuring easy welding of the balloon and a good stiffness at that level. These and other objects will become readily apparent from the following detailed description with reference to the accompanying drawings which show, diagrammatically and by way of example only, a preferred embodiment of the invention.

BRIEF DESCRIPTION OF THE DRAWINGS

FIG. 1 is a longitudinal cut out of this embodiment; and
FIG. 2 is a section according to line I-I of FIG. 1.

DETAILED DESCRIPTION OF THE INVENTION

The interventional catheter shown in FIGS. 1 and 2 comprises a catheter tube 1 which is formed, in this embodiment, of two superposed continuous layers 2 and 3 extending all over the length of the tube 1; this tubing, which may be achieved by the known co-extrusion technology, i.e. by extruding the outer layer over the inner layer, is comprised of a polyethylene, preferably a high density polyethylene, for the inner layer 2, and of a polyamide for the outer layer 3. The inner layer 2 thus forms a longitudinal lumen 12 with a very low friction coefficient, lower than that of the material forming the outer layer 3, and a non kinking capacity, while the outer layer 3 is easily weldable to the materials commonly used for making balloons for angioplasty and the like.

Over the distal portion of the catheter tube 1 is positioned a balloon 4 the distal end 5 of which is sealed to the outer layer 3 of the catheter tube 1, for instance by welding.

A tube 7 is arranged over the catheter tube 1, at a radial distance thereof, thus defining an inflating lumen 8 for the balloon 4. The proximal end 6 of the balloon 4 is welded onto the distal end of said tube 7.

The tube 7 is exemplified here as being made of two tubes 9 and 10 longitudinally affixed to one another. Preferably the tube 9 and 10 shall be made of a polyamide to achieve easy fixing by welding procedures and to obtain a stepped stiffness. The proximal end of tube 10 is connected to conventional fittings (not shown) to feed the balloon and drive the catheter assembly. Inside the catheter tube 1 is placed a guide wire 11 in sliding fit within the inner layer 2 forming the longitudinal lumen 12.

As a variant, the two tubes configuration of the tube 7 may be replaced by a single tube or by a configuration having more than two longitudinally affixed tubes.

What is claimed is:

1. A catheter comprising:

an outer tubular member having an inner surface defining a lumen extending between a proximal end and a distal end of the outer tubular member, wherein a first portion of the outer tubular member has a first stiffness and a second portion of the outer tubular member has a second stiffness less than the first stiffness;

an inner tubular member having a proximal end, a distal end and a lumen extending therethrough, the inner tubular member disposed within the lumen of the outer tubular member, the inner tubular member having an inner layer defining an inner surface of the inner tubular member and an outer layer defining an outer surface of the inner tubular member;

an inflation lumen defined between the outer surface of the inner tubular member and the inner surface of the outer tubular member; and a balloon attached to the distal end of the outer tubular member and the distal end of the inner tubular member, wherein the balloon is in fluid communication with the inflation lumen;

wherein the inner layer of the inner tubular member is disposed partially in the outer tubular member and partially in the balloon;

wherein the outer layer of the inner tubular member is disposed partially in the outer tubular member and partially in the balloon; and wherein the inner layer of the inner tubular member is separated from the balloon by the outer layer of the inner tubular member.

2. The catheter of claim 1, wherein the inner surface of the inner tubular member has a first coefficient of friction and the outer surface of the inner tubular member has a second coefficient of friction greater than the first coefficient of friction.

3. The catheter of claim 1, wherein the outer tubular member includes a plurality of segments joined together.

4. The catheter of claim 1, wherein the inner tubular member is adapted to prevent kinking, and the outer tubular member is adapted to provide stiffness for the catheter.

5. The catheter of claim 1, wherein the inner tubular member comprises high density polyethylene.

6. The catheter of claim 1, wherein the outer layer of the inner tubular member comprises polyamide.

7. The catheter of claim 1, wherein the inner layer of the inner tubular member comprises high density polyethylene and the outer layer of the inner tubular member comprises polyamide.

8. The catheter of claim 1, wherein the inner layer of the inner tubular member consists essentially of high density polyethylene and the outer layer of the inner tubular member consists essentially of polyamide.

9. The catheter of claim 1, wherein the inner layer of the inner tubular member comprises a first material and the outer layer of the inner tubular member comprises a second material.

10. The catheter of claim 1, wherein the inner tubular member is disposed coaxially within the outer tubular member.

11. The catheter of claim 1, wherein the first portion of the outer tubular member is located proximal of the second portion.

12. The catheter of claim 1, wherein the distal end of the inner tubular member extends distal of the distal end of the outer tubular member.

13. A catheter comprising:

an outer tubular member having a proximal end, a distal end and a lumen extending therethrough, wherein a first portion of the outer tubular member has a first stiffness and a second portion of the outer tubular member has a second stiffness less than the first stiffness;

an inner tubular member having a proximal end, a distal end and a lumen extending therethrough, the inner tubular member disposed within the lumen of the outer tubular member, the inner tubular member including an inner layer of material comprising high density polyethylene and an outer layer of material comprising polyamide; and a balloon attached to the distal end of the outer tubular member and the distal end of the inner tubular member;

wherein the inner layer of the inner tubular member is separated from the balloon by the outer layer of the inner tubular member.

14. The catheter of claim 13, wherein the inner layer and the outer layer of the inner tubular member are co-extruded.

15. The catheter of claim 13, wherein the inner layer and the outer layer of the inner tubular member are congruent in length.

16. The catheter of claim 13, wherein the outer tubular member includes a plurality of segments joined together.

17. The catheter of claim 13, wherein the distal end of the inner tubular member extends distal of the distal end of the outer tubular member.

18. The catheter of claim 13, wherein the outer tubular member comprises polyamide.

19. The catheter of claim 13, wherein the first portion of the outer tubular member is located proximal of the second portion.

* * * * *

UNITED STATES PATENT AND TRADEMARK OFFICE
CERTIFICATE OF CORRECTION

PATENT NO.        : 7,635,347 B2                                         Page 1 of 1
APPLICATION NO. : 11/229301
DATED             : December 22, 2009
INVENTOR(S)       : Gerhard Kastenhofer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 835 days.

Signed and Sealed this

Ninth Day of November, 2010

David J. Kappos
*Director of the United States Patent and Trademark Office*